United States Patent
Khoubnazar

(10) Patent No.: US 8,425,482 B2
(45) Date of Patent: Apr. 23, 2013

(54) ELASTICIZED ABSORBENT ARTICLE

(76) Inventor: Nayereh Khoubnazar, Los Angeles, CA (US)

( * ) Notice: Subject to any disclaimer, the term of this patent is extended or adjusted under 35 U.S.C. 154(b) by 592 days.

(21) Appl. No.: 12/708,086

(22) Filed: Feb. 18, 2010

(65) Prior Publication Data

US 2010/0280470 A1 Nov. 4, 2010

(51) Int. Cl.
*A61F 13/15* (2006.01)

(52) U.S. Cl.
USPC ....... 604/385.09; 604/349; 604/353; 604/354

(58) Field of Classification Search ............ 604/385.09, 604/346–347, 349–354
See application file for complete search history.

(56) References Cited

U.S. PATENT DOCUMENTS

| | | | |
|---|---|---|---|
| 2,445,220 A * | 7/1948 | Isaacson | 604/349 |
| 2,864,369 A * | 12/1958 | Morrow | 604/353 |
| 4,601,716 A * | 7/1986 | Smith | 604/349 |
| 4,863,448 A * | 9/1989 | Berg | 604/349 |
| 2002/0177825 A1 * | 11/2002 | Scovel | 604/353 |
| 2004/0106909 A1 * | 6/2004 | Browning | 604/349 |
| 2004/0111073 A1 * | 6/2004 | Hermansson et al. | 604/349 |
| 2006/0149196 A1 * | 7/2006 | Bjornberg et al. | 604/349 |
| 2007/0149935 A1 * | 6/2007 | Dirico | 604/347 |

* cited by examiner

*Primary Examiner* — Lynne Anderson

(74) *Attorney, Agent, or Firm* — Musick Peeler, LLP; Reid Dammann, Esq.

(57) ABSTRACT

An elasticized flexible absorbent article for minor urinary incontinence is provided. The elasticized flexible absorbent article comprises an inner permeable hydrophilic layer, an absorbent layer having a first side and a second side, the first side of the absorbent layer at least partially bonded to the inner permeable hydrophilic layer, and an impermeable outer cover having a first side, a second side, and an elastic portion, the first side of the impermeable outer cover at least partially bonded to the second side of the absorbent layer, the elastic portion provided along an outer edge of the impermeable outer cover, the elasticized flexible absorbent article adapted to encompass an end portion of a male genital region.

16 Claims, 3 Drawing Sheets

ELASTICIZED ABSORBENT ARTICLE

BACKGROUND

1) Field of the Invention

The invention relates to a medical device for urinary leakage. More particularly, the invention relates to an absorbent device to assist in the prevention of minor urinary leakage.

2) Discussion of the Related Art

Urinary incontinence is defined as the inability to fully control urination. This condition can be temporary or permanent depending on the underlying cause, and can comprise either a major or minor amount of leakage. There are many types of urinary incontinence caused by a wide variety of conditions such as neurological disorders, Diabetes Mellitus, prostate problems, aging, surgery, and urinary tract infections. Recent estimates indicate that roughly 5 million men in the United States have some form of urinary incontinence.

Any disease, condition, or injury that damages nerves can lead to urination problems. For example, a spinal cord injury may affect bladder emptying by interrupting the nerve signals required for bladder control.

Prostate problems can also lead to urinary incontinence. As a man ages, the prostate gland enlarges, increasing pressure and squeezing the urethra, affecting the flow of the urine stream.

However, urinary incontinence is a treatable problem and can be achieved through several means. One method is through urinary incontinence surgery. This method includes a variety of procedures, from a minimally invasive injection of bulking agents to major surgical intervention. The more invasive the surgery, the higher the risk of complications. For instance, the surgery itself may give rise to different urinary and genital problems, such as urinary retention, development of an overactive bladder, pelvic organ prolapse, urinary tract infections, and difficult or painful intercourse.

Another method of treatment of urinary incontinence is through the use of medication. Medication can reduce leakage by inhibiting contractions of an overactive bladder or by relaxing muscles, leading to more complete bladder emptying during urination. The medication can also act by tightening muscles at the bladder neck and urethra, preventing leakage. However, like urinary incontinence surgery, medication can produce unwanted side effects. A few side effects include dry eyes and mouth, headaches, constipation, rapid heart rate, confusion, and forgetfulness.

Currently, there are a variety of absorbent products on the market which aid in urinary incontinence. These products provide an alternative to those who are risk adverse. These kinds of products generally include undergarments, protective underwear, adult pull ups, under pads, and garment liners.

While these products aid the problem, they are bulky, cumbersome, and uncomfortable. It is not uncommon for users to buy larger sized clothing to accommodate the additional the bulk and to eliminate the embarrassing external appearance many of these products cause.

Further, these absorbent products are generally tailored for major urinary leakage, and are generally seen as overkill for those with minor incontinence problems. Therefore, those with minor urinary leakage are forced to either undergo the unwanted risks and side effects of surgery and medication or undergo the embarrassment caused by using products that are not specifically directed to the treatment of this minor problem.

BRIEF DESCRIPTION OF THE DRAWINGS

The invention is described by way of example with reference to the accompanying drawings wherein.

DETAILED DESCRIPTION OF THE INVENTION

As used herein, the term "absorbent article" refers to devices which absorb and contain body exudates and, more specifically, refers to devices which are placed against or in proximity to the body of the wearer to absorb and contain the various exudates discharged from the body.

The invention described herein is multilayered. Each layer is bonded to the next layer in some fashion, in that, each layer is comprised of a first and a second side and is bonded to the respective side accordingly. As such, the term "bonded" refers to the joining, adhering, affixing, connecting, attaching, threading or the like, through chemical, mechanical or electrical avenues, of at least two elements of an absorbent article, such that the elements tend to be and remain bonded during normal use conditions of the absorbent article.

Furthermore, while the described layers can include certain means described above for bonding, these layers can also encompass types of bonding used by other non-layered elements of the invention. These other non-layered elements can be bonded by, and generally include fastening means like belts, buckles, buttons, Velcro (R), rivets, tabs or other mechanical or fabric fasteners. These structures can serve to connect two or more elements in the invention. A wide variety of means are possible, and it is to be understood that such embodiments are merely illustrative and not restrictive of the current invention.

Figure 1:
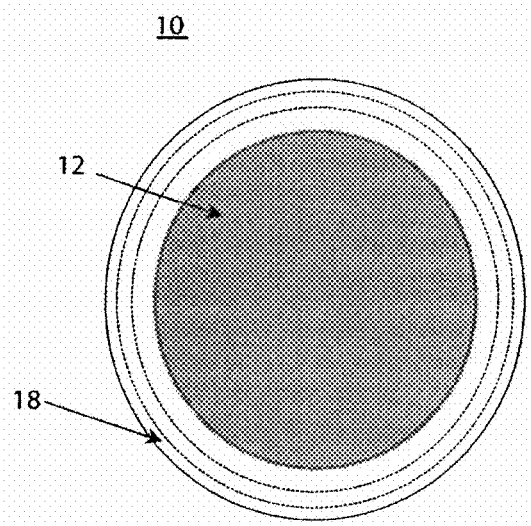
FIG. 1 illustrates a top perspective of an elasticized flexible absorbent article.
Figure 2:
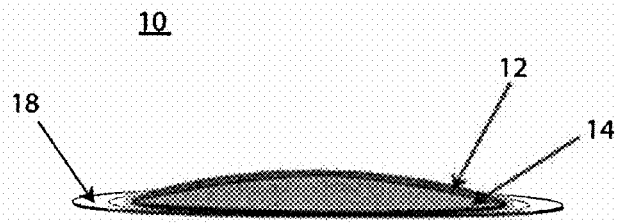
FIG. 2 illustrates a side perspective of the elasticized flexible absorbent article.

FIGS. 1 and 2 illustrate an elasticized flexible absorbent article 10. The elasticized flexible absorbent article 10 is comprised of an inner permeable hydrophilic layer 12, an absorbent layer 14 (illustrated in FIG. 2), and an impermeable outer cover 18. A second side of the inner permeable hydrophilic layer 12 is partially bonded to a first side of the absorbent layer 14. A second side of the absorbent layer 14 is partially bonded to a first side of the impermeable outer cover 18.

The inner permeable hydrophilic layer 12 can be comprised of a variety of natural and/or synthetic fibers or polymers. As such, in an embodiment, the inner permeable hydrophilic layer 12 is made of particles of an acrylic acid derivative, such as sodium acrylate, potassium acrylate, or an alkyl acrylate or other polymer chain. The particles retain many times their weight in water and are designed to interact with water molecules. These polymer chains can cross-link, forming a matrix functioning to absorb larger amounts of water. Depending on the cross-linking, these polymers are referred to as hydrogels, superabsorbents, or hydrocolloids.

The absorbent layer 14 is the core of the elasticized flexible absorbent article 10. The function of the absorbent layer 14 is to absorb and retain moisture from the inner permeable hydrophilic layer 12. The absorbent layer 14 draws moisture from the inner hydrophilic layer 12 and disperses the moisture throughout the matrix in order to reduce leakage.

Figure 3:
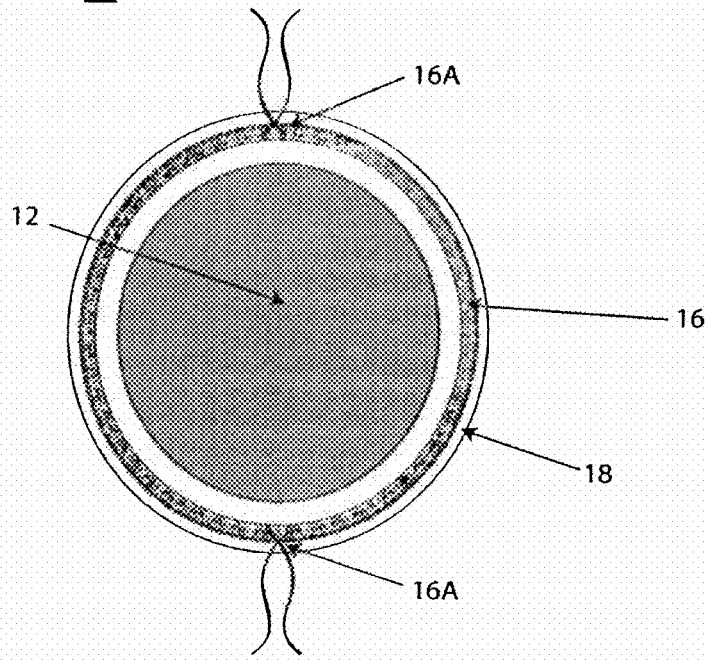
FIG. 3 illustrates a top perspective of the elasticized flexible absorbent article with an elastic portion having at least one securing strap.

FIG. 3 illustrates the elasticized flexible absorbent article 10 in more detail. The impermeable outer cover 18 includes a first side, a second side, and an elastic portion 16. The first side of the impermeable outer cover 18 is at least partially bonded to the second side of the absorbent layer 14 (illustrated in FIG. 2). The elastic portion 16 is provided along a circumferential outer edge of the impermeable outer cover 18 and includes at least one securing strap 16A.

Used to improve the fit of the elasticized flexible absorbent article 10, the elastic portion 16 is made of polyurethane or polyester foam, synthetic rubber or Lycra. The elastic portion 16 is can exist throughout the circumferential outer edge of the absorbent layer 14, or in an embodiment, can be intermittently dispersed. In another embodiment, the elastic portion 16 can exist at any distance along a radius or diameter of the impermeable outer cover 18. Therefore, given its structure, the function of the elastic portion 16 is to provide a user a layer of comfort without the need for additional supports for attachment. Further, as a tertiary measure, the elastic portion 16 prevents leakage to the extent the absorbent layer 14 and the inner permeable hydrophilic layer 12 are saturated.

FIG. 3 also illustrates the at least one securing strap 16A. The at least one securing strap 16A provides an additional level of comfort to the user and, at the same time, supports the functionality of the elastic portion 16 in preventing leakage. In an embodiment, the at least one securing strap 16A can be placed on the second side of the impermeable outer cover 18, allowing the user easy access to fit the elasticized flexible absorbent article 10. The at least one securing strap 16A, in an embodiment, can be made of materials similar to the elastic portion 16.

The impermeable outer cover 18, in an embodiment, is hydrophobic and flexible. In another embodiment, the impermeable outer layer 18 is made of non-woven fabric, which can include plastic resins. The plastic resins can include nylon, polyester, polyethylene, or polypropylene, and are assembled by interlocking the plastic fibers.

The impermeable outer cover 18 functions to prevent leakage and to provide a flexible structure to the user by encompassing the absorbent layer 14, via the impermeable outer layer 18 first side and the inner permeable hydrophilic layer 12. Further, the impermeable outer cover 18 houses the elastic portion 16 as described herein and the at least one securing strap 16A, which function to secure the impermeable outer cover 18 to fit the uniqueness of each user.

The respective layers comprising the elasticized flexible absorbent article 10 can take a variety of shapes depending on the usage involved. In an embodiment, the absorbent layer 14, inner permeable hydrophilic layer 12, and the impermeable outer cover 18 are concentric sphere shapes, allowing for a more rounded fit during use, as described herein. However, a wide variety of shapes and sizes can be possible, and as such, it is to be understood that such embodiments are merely illustrative and not restrictive.

Figure 4:
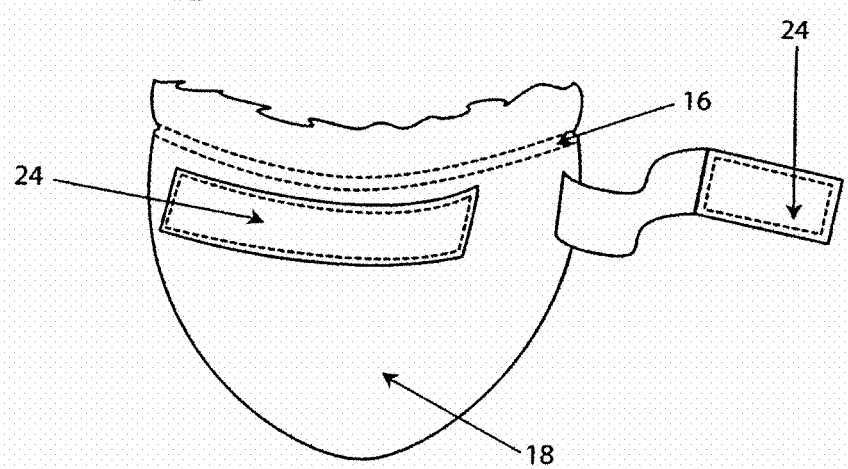
FIG. 4 illustrates a side perspective of the elasticized flexible absorbent article adapted to encompass an end portion of a male genital region.

FIG. 4 illustrates an embodiment of the elastic flexible absorbent article 10 in detail. In this embodiment, the impermeable outer layer 18 is able to encompass an end portion of a male genital region. This feature is specifically enhanced by the elastic portion 16.

The genital region is made up of the glans, foreskin, and shaft, any of which, separately or together, comprise the end portion of the genital region. In an embodiment, the elastic flexible absorbent article 10 extends over the glans and shaft of the penis. In another embodiment, elastic flexible absorbent article 10 extends over just the glans portion. In both embodiments, the elastic portion 16 contacts the foreskin of the penis, allowing for the elastic flexible absorbent article 10 to fit comfortably and circumferentially, against the end portion of the penis.

As illustrated in FIG. 4, the impermeable outer layer 18 includes a fastening member 24. The fastening member 24 is at least partially bonded to the second side of the impermeable outer layer 18. In addition to the at least one securing strap 16A, the fastening member 24 is provided for an additional level of comfort to the user in fit, as well as functionality in retaining moisture from the user.

In an embodiment, the fastening member 24 can consist of a Velcro(R) attachment, wherein a plurality of straps exist for fastening or securing. In another embodiment, the fastening member 24 can comprise a felt or soft fabric buckle. However, generally, the fastening member 24 can be comprised of any securing feature which includes materials that are generally not hard or rigid in fashion, and function to fasten, connect and/or tighten. A wide variety of means for securing are possible, as such, it is understood that such embodiments are merely illustrative and not restrictive of the current invention.

Figure 5:
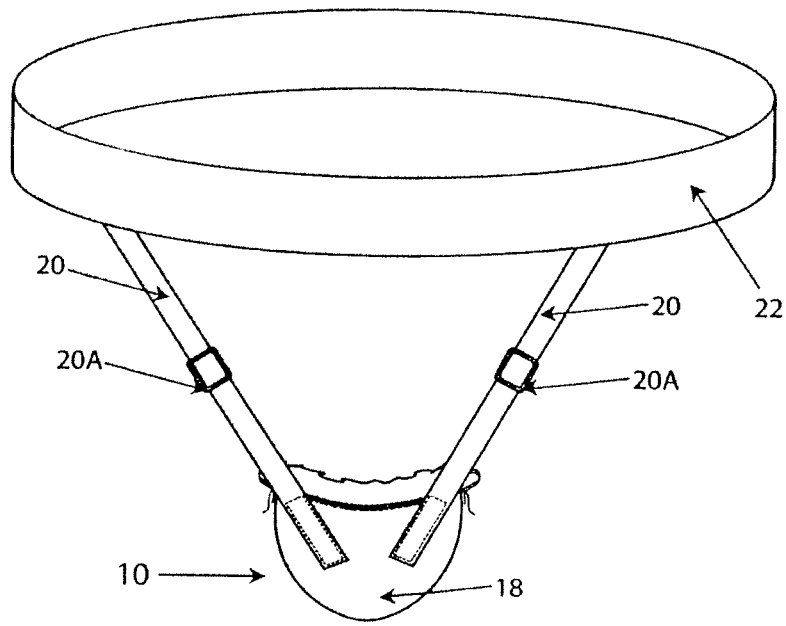
FIG. 5 illustrates the elasticized flexible absorbent article having a waist portion adapted to be secured around the waist of a user.

FIG. 5 illustrates an embodiment of the elastic flexible absorbent article 10. In this embodiment, the elasticized flexible absorbent article 10 is partially bonded to at least one supporting member 20 via the second side of the impermeable outer cover 18, according to means described herein. The at least one supporting member 20 is further partially bonded to a waist portion 22. The waist portion 22 is secured around the waist of the user. As further illustrated in FIG. 5, in an embodiment, the at least one supporting member 20 can encompass an adjustment member 20A for adjusting to a specific length for the user.

The waist portion 22 and the at least one supporting member 20 can be elastic. In an embodiment, the materials comprising the waist portion 22, as well as other elements of the invention, can be disposable. However, a wide variety of materials can be used, and are possible, and as such, it is understood that such embodiments are merely illustrative and not restrictive.

Figure 6:
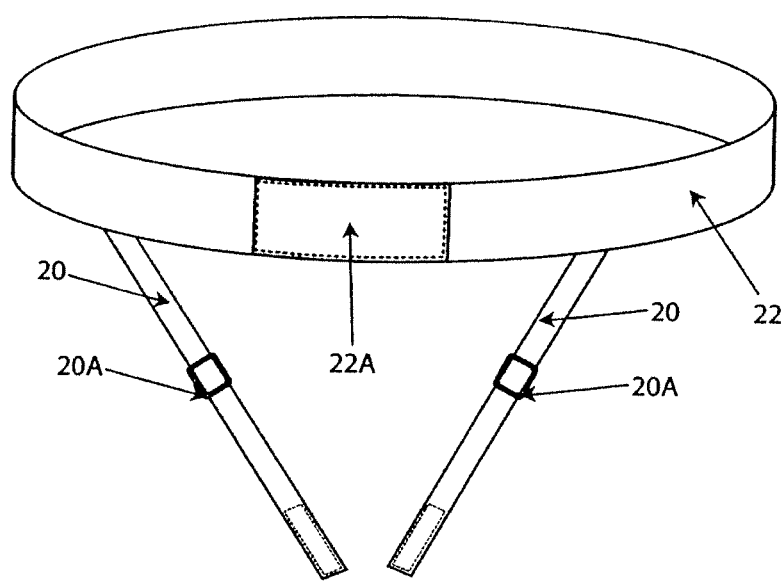
FIG. 6 illustrates the elasticized flexible absorbent article having the waist portion include a securing member.

FIG. 6 illustrates an embodiment of the waist portion 22 in detail. In this embodiment, the waist portion 22 includes a securing member 22A. The securing member 22A is partially bonded to the waist portion 22 and is provided for ease of adjustment and comfort during use. The securing member 22A can encompass a variety of fastening means described herein, as well as those known in the art, with the primary factors being comfort and ease of use.

The function of the at least one supporting member 20 is to provide an additional level of security and comfort to the user. The at least one supporting member 20 can play, in an embodiment, a particular role in securing the elastic flexible absorbent article 10 to the end portion of a male genital region, wherein the elastic flexible absorbent article 10 is encompassing only the glans penis portion of the male genitals. In that, because of the decreased amount of contact with the foreskin, the at least one supporting member 20 provides added security, if needed. Of course, as stated herein, each user is unique and must be accommodated accordingly.

The connection between the at least one supporting member 20 and the elastic flexible absorbent article 10, specifically, the impermeable outer layer 18, in an embodiment, can be bonded or made through a variety of fastening means including Velcro (R), thread, and fabric. Further, the connection between the at least one supporting member 20 and the waist portion 22, can be similar to that of the connection between the elasticized flexible absorbent article 10 and the at least one supporting member 20. As such, a wide variety of means can be possible, and as such, it is to be understood that such embodiments are merely illustrative and not restrictive.

In use, the user places the elasticized flexible absorbent article 10 over the end portion of the user's male genital region. The inner permeable hydrophilic layer 12 is the layer closest to the urethra of the genitals or the tip of the penis. Generally, a void or space is present between the inner permeable hydrophilic layer 12 and the urethra or the tip of the penis.

The elastic portion 16 of the impermeable outer cover 18 secures the inner permeable hydrophilic layer 12, absorbent layer 14, and the impermeable outer cover 18 to the end portion of the male genital region. If the elastic portion 16 is unable to secure tightly enough for the user, the user is able to adjust, using the at least one securing strap 16A, for additional comfort and security. Additionally, as described herein, in an embodiment, the user is able to adjust the fastening member 24 for additional comfort and fit.

As described herein, in an embodiment, the user is able to use the elastic flexible absorbent article 10 with the at least one supporting member 20 and the waist portion 22. In this embodiment, the user secures the waist portion 22 around the waist. The user then places the elasticized flexible absorbent article 10 over the user's end portion of the male genital region, and is otherwise consistent with the use described above.

In this embodiment, the at least one supporting member 20 can either be of the proper length to provide support to the elasticized flexible absorbent article 10 on the user, or as indicated in another embodiment, can be adjusted via the adjustment member 20A, to the specifics of the user. Further, in an embodiment, and for additional comfort and fit, the user is able to use the securing member 22A, allowing the waist portion 22 to bifurcate, allowing the user to step into, instead of sliding on, the waist portion 22.

An advantage of the invention is its number of elements and methods of attachment. The elastic flexible absorbent article is geared towards ease of use, removal, and disposal after leakage. To accomplish this end, the invention includes elements no more than necessary to solve the problem of controlling minor urinary incontinence. Further, each element is able to be secured and detached using minimal effort.

Further still, because of the size of the elastic flexible absorbent article 10, an advantage of the invention is that it allows the user to wear their pre-urinary incontinence wardrobe. This advantage alleviates the need to buy additional clothing and the embarrassment felt with the current products.

The invention is able to provide this advantage because it is specifically tailored to the user with minor urinary incontinence. The layers of the invention are specifically adapted to collect a volume of material, therefore, the thickness is no more than necessary under the circumstances. Further, the size of such layers are small enough to encompass just the end portion of male genitals, encompassing or involving, no more or less than absolutely necessary. This invention also provides the additional advantage of allowing the user to carry the invention, unlike other bulky products, on their person.

Another advantage of the invention is the adjustment ability associated with many of the elements of the invention. This advantage can be seen from the elastic portion 16 of the invention to the waist portion 22, as well as the at least one securing strap 16A, the fastening member 24, the securing member 22A, and the adjustment member 20A. These features aid in providing comfort and fit to a wide variety of users.

While certain exemplary embodiments have been described and shown in the accompanying drawings, it is to be understood that such embodiments are merely illustrative and not restrictive of the current invention, and that this invention is not restricted to the specific constructions and arrangements shown and described since modification can occur to those ordinarily skilled in the art.

What is claimed:

1. An elasticized flexible absorbent article for minor urinary incontinence, comprising:
   an inner permeable hydrophilic layer;
   an absorbent layer having a first side and a second side, the first side of the absorbent layer at least partially bonded to the inner permeable hydrophilic layer; and
   an impermeable outer cover having a first side, a second side, and an elastic portion;
   at least one securing strap within the elastic portion, the first side of the impermeable outer cover at least partially bonded to the second side of the absorbent layer, the elastic portion provided along an outer edge of the impermeable outer cover, the elasticized flexible absorbent article adapted to encompass an end portion of a male genital region.

2. The elasticized flexible absorbent article of claim 1 wherein the absorbent layer is comprised of at least one of synthetic fiber and natural fiber.

3. The elasticized flexible absorbent article of claim 2 wherein the absorbent layer is comprised of superabsorbent polymer.

4. The elasticized flexible absorbent article of claim 1 wherein the absorbent layer, the inner permeable layer, and the impermeable outer cover are concentric spheres.

5. The elasticized flexible absorbent article of claim 4 wherein the elastic portion is provided along a circumferential outer edge of the outer cover.

6. The elasticized flexible absorbent article of claim 1 wherein the impermeable outer cover is comprised of nonwoven material comprising at least one of nylon, polyester, polyethylene, or polypropylene.

7. The elasticized flexible absorbent article of claim 1, the impermeable outer cover including a fastening member partially bonded to the second side of the impermeable outer cover.

8. The elasticized flexible absorbent article of claim 1 wherein the absorbent layer, the inner permeable layer, and the impermeable outer cover are shaped to extend over the glans and shaft of a penis.

9. An elasticized flexible absorbent article for minor urinary incontinence, comprising:
   a waist portion secured around a waist of a user, the waist portion including a securing member around the waist of the user;
   at least one supporting member at least partially bonded to the waist portion;
   an inner permeable hydrophilic layer;
   an absorbent layer having a first side and a second side, the first side of the absorbent layer at least partially bonded to the inner permeable hydrophilic layer; and
   an impermeable outer cover having a first side, a second side, and an elastic portion;
   at least one securing strap within the elastic portion, the first side of the impermeable outer cover at least partially bonded to the second side of the absorbent layer, the at least one supporting member at least partially bonded to the second side of the impermeable outer cover, the elastic portion provided along an outer edge of the impermeable outer cover, the elasticized flexible absorbent article adapted to encompass an end portion of a male genital region.

10. The elasticized flexible absorbent article of claim 9 wherein the absorbent layer is comprised of at least one of synthetic fiber and natural fiber.

11. The elasticized flexible absorbent article of claim 10 wherein the absorbent layer is comprised of superabsorbent polymer.

12. The elasticized flexible absorbent article of claim 7 wherein the absorbent layer, the inner permeable layer, and the impermeable outer cover are concentric spheres.

13. The elasticized flexible absorbent article of claim 12 wherein the elastic portion is provided along a circumferential outer edge of the impermeable outer cover.

14. The elasticized flexible absorbent article of claim 9 wherein the impermeable outer cover is comprised of nonwoven material comprising at least one of nylon, polyester, polyethylene, or polypropylene.

15. The elasticized flexible absorbent article of claim 9, the impermeable outer cover including a fastening member partially bonded to the second side of the impermeable outer cover.

16. The elasticized flexible absorbent article of claim 9 wherein the absorbent layer, the inner permeable layer, and the impermeable outer cover are shaped to extend over the glans and shaft of a penis.

* * * * *